United States Patent [19]

Wesson et al.

[11] Patent Number: 4,994,046
[45] Date of Patent: Feb. 19, 1991

[54] NEEDLE GUARD FOR SYRINGE

[75] Inventors: Vann T. Wesson, 4155 Caminito Cassis, San Diego, Calif. 92122; Jean P. Wesson, San Diego; Thomas J. Ryan, Del Mar, both of Calif.

[73] Assignee: Vann T. Wesson, Encinitas, Calif.

[21] Appl. No.: 455,938

[22] Filed: Dec. 22, 1989

Related U.S. Application Data

[63] Continuation of Ser. No. 292,375, Dec. 30, 1988, abandoned, which is a continuation-in-part of Ser. No. 176,653, Apr. 1, 1988, abandoned.

[51] Int. Cl.$^5$ .............................. A61M 5/32
[52] U.S. Cl. ........................ 604/198; 604/263; 128/919
[58] Field of Search .............. 604/192, 197, 158, 110, 604/263; 128/763–765

[56] References Cited

U.S. PATENT DOCUMENTS

| | | |
|---|---|---|
| 2,571,653 | 10/1951 | Bastien . |
| 3,658,061 | 4/1972 | Hall ..................... 604/263 |
| 4,232,669 | 11/1980 | Nitshke ..................... 604/263 |
| 4,356,822 | 11/1982 | Winstead-Hall . |
| 4,425,120 | 1/1984 | Sampson et al. .............. 604/198 |
| 4,573,976 | 3/1986 | Samson et al. .............. 604/198 |
| 4,631,057 | 12/1986 | Mitchell ..................... 604/198 |
| 4,655,751 | 4/1987 | Harbaugh ..................... 604/198 |
| 4,659,330 | 4/1987 | Nelson et al. ................ 604/263 |
| 4,664,259 | 5/1987 | Landis ..................... 604/192 |
| 4,664,654 | 5/1987 | Strauss ..................... 604/198 |
| 4,681,567 | 7/1987 | Masters et al. .............. 604/198 |
| 4,702,738 | 10/1987 | Spencer ..................... 604/198 |
| 4,702,739 | 10/1987 | Milorad ..................... 604/198 |
| 4,723,943 | 2/1988 | Spencer ..................... 604/263 |
| 4,726,466 | 2/1988 | Cooper ..................... 206/366 |
| 4,738,663 | 4/1988 | Bogan ..................... 604/198 |
| 4,743,233 | 5/1988 | Schneider ..................... 604/192 |
| 4,795,443 | 1/1989 | Permenter et al. .............. 604/198 |
| 4,826,491 | 5/1989 | Schramm ..................... 604/263 |
| 4,915,696 | 4/1990 | Feimer ..................... 604/192 |
| 4,946,447 | 8/1990 | Hardcastle et al. .............. 604/198 |

FOREIGN PATENT DOCUMENTS 2178322  2/1987  United Kingdom .............. 604/263

Primary Examiner—C. Fred Rosenbaum
Assistant Examiner—Mark O. Polutta
Attorney, Agent, or Firm—Baker, Maxham Jester & Meador

[57]   ABSTRACT

An elongate cylindrical body portion and a spoon-shaped shield member are injection molded as a single unitary piece of transparent polypropylene. The cylindrical body portion has a longitudinally extending slot so that it can be readily snapped around the barrel of a syringe. The spoon-shaped member extends from the forward end of the body portion. This member can deflect transversely from an un-deflected non-use configuration to a slightly deflected in-use configuration to permit the needle to extend therebeyond when the guard is installed with the body portion in a retracted position relative to the barrel of the syringe. When the body portion of the guard is manually slid to an extended position relative to the syringe barrel, the spoon-shaped member returns to its un-deflected configuration and the tip of the needle is engaged by a plurality of ribs formed on an inner wall of the spoon-shaped member. The tip of the needle is thus concealed and accidental puncture thereby is avoided.

10 Claims, 5 Drawing Sheets

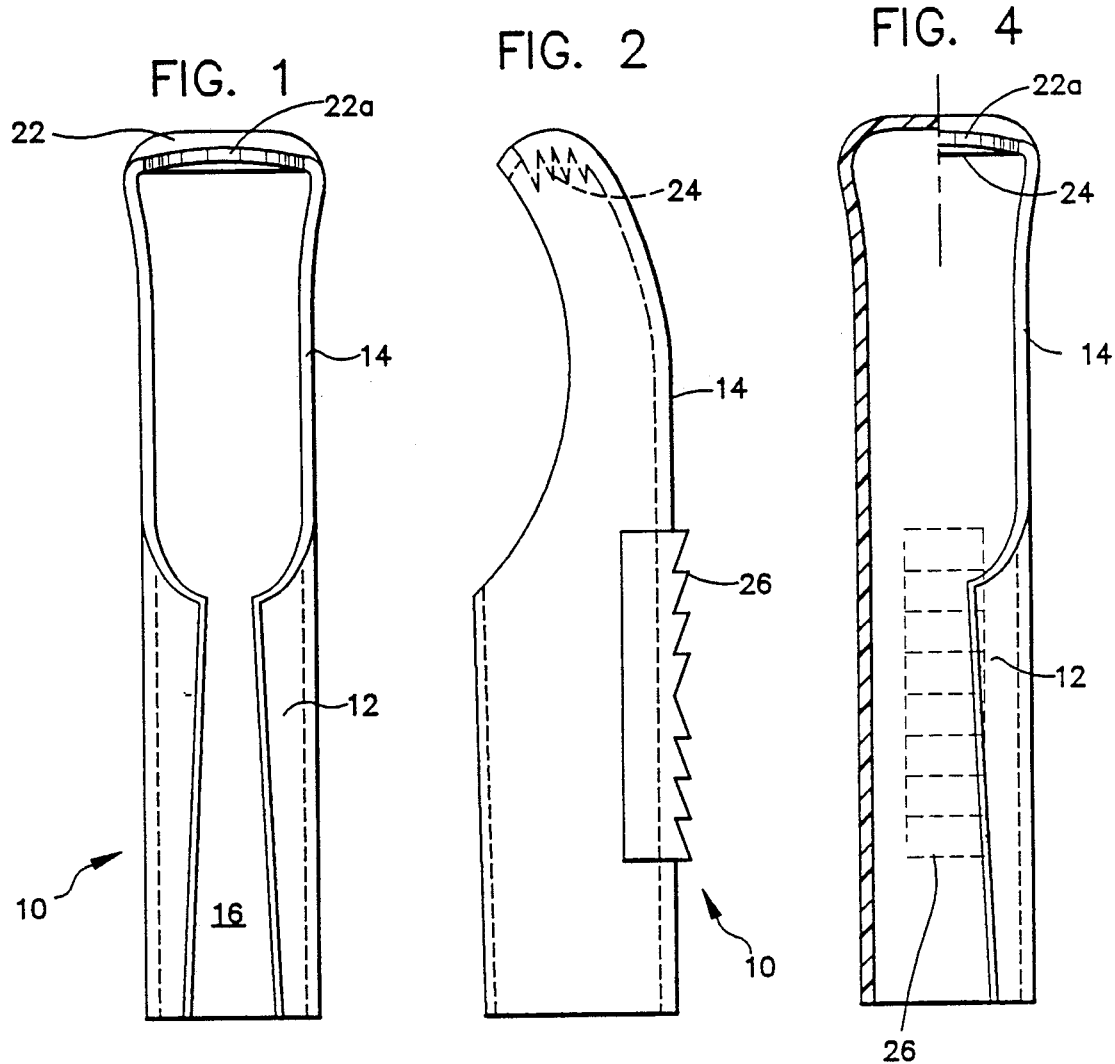
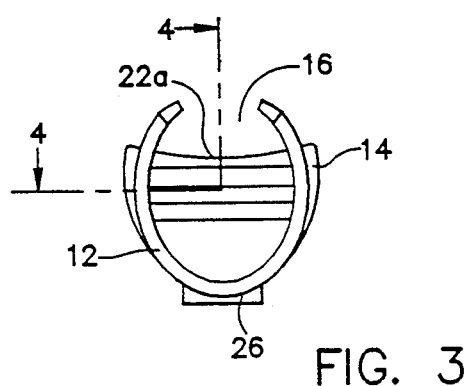

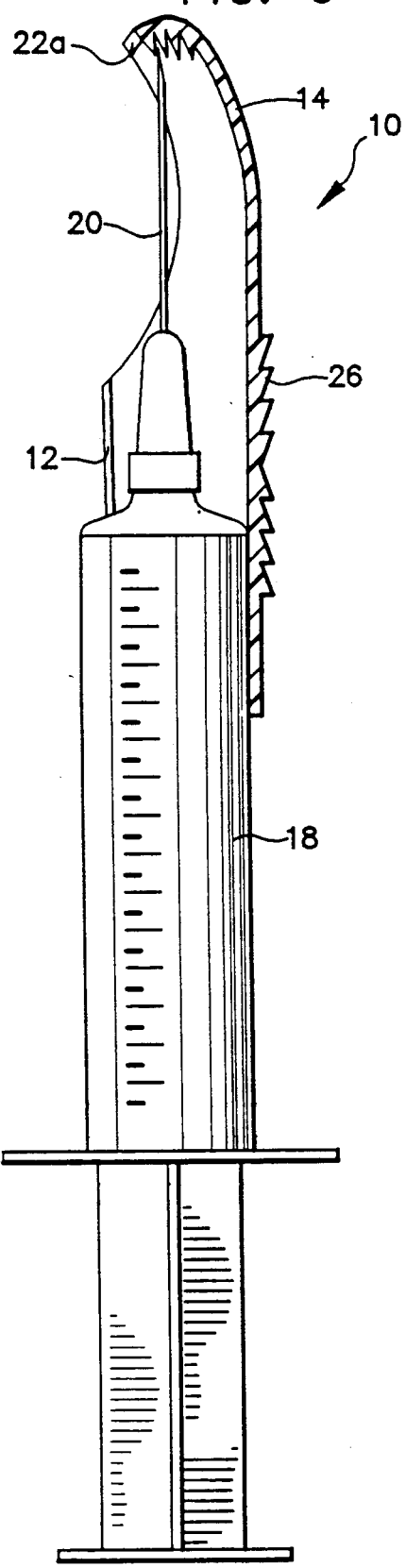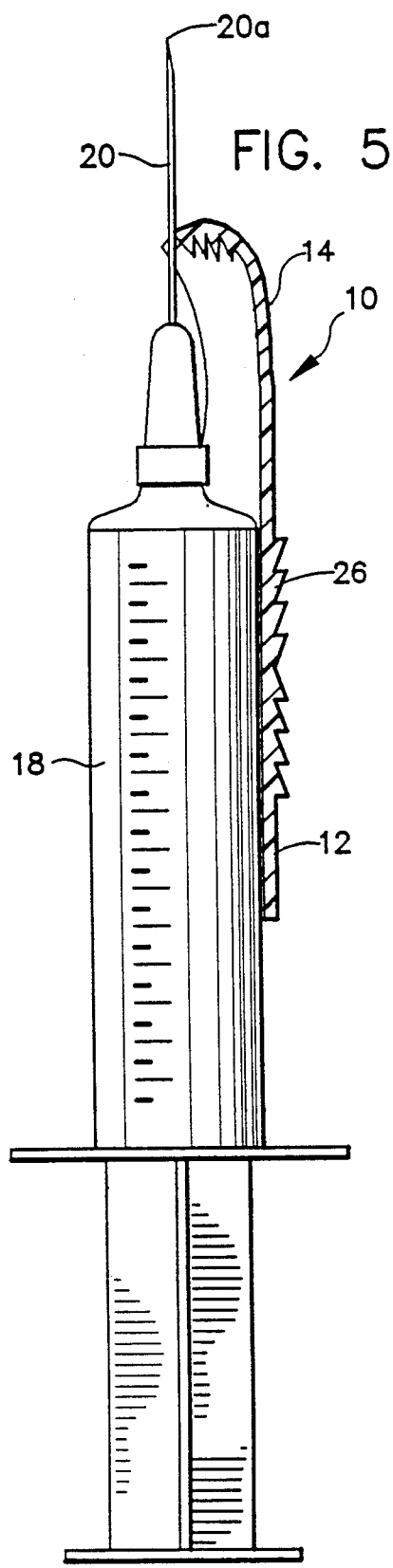

NEEDLE GUARD FOR SYRINGE

CROSS-REFERENCE TO RELATED APPLICATION

This is a continuation of application Ser. No. 07/292,375, filed Dec. 30, 1988, abandoned, which is a continuation-in-part of the identically entitled U.S. Pat. Application Ser. No. 176,653 filed April 1, 1988 abandoned naming Vann T. Wesson and Thomas J. Ryan as co-inventors.

BACKGROUND OF THE INVENTION

The present invention relates to medical devices, and more particularly, to a guard for a syringe that will protect the health care professional from inadvertently sticking himself or herself with the needle after administering medication or drawing blood with the syringe.

Accidental needle puncture frequently occurs when a nurse or physician attempts to recap a needle after giving an injection or drawing blood from a patient. Needlestick injuries may transmit such infectious particles as hepatitis B virus, non-A and non-B hepatitis virus, and human immunodeficiency virus (HIV), with disastrous consequences.

U.S. Pat. No. 2,571,653 of Bastein discloses a cylindrical sheath that surrounds the syringe barrel and extends and retracts relative thereto. The needle can extend through a hole in the distal end of the sheath. The tip of the needle is recessed into the end of the sheath when the same is fully retracted. A latch on the inner surface seats in an annular groove in the sheath to lock the sheath in its fully extended position.

U.S. Pat. No. 4,425,120 of Sampson et al. discloses a cylindrical needle guard which surrounds the barrel of the syringe and moves to an extended position to shield the tip of the needle. Locking of the guard is accomplished by a track on the internal surface of the guard and track engaging members on the barrel.

U.S. Pat. No. 4,356,822 of Winstead-Hall discloses a cylindrical cap member that surrounds and reciprocates longitudinally along the barrel of a syringe. A frangible end closure is provided on the end of the cap member closest to the tip of the needle. A series of formations on the barrel engage a series of formations on the cap to permit the cap to be secured at different longitudinal positions relative to the barrel to thereby expose varying amounts of the needle.

U.S. Pat. No. 4,573,976 of Sampson et al. discloses another releasably retained, longitudinally extensible cylindrical guard that surrounds the barrel of a syringe.

U.S. Pat. No. 4,631,057 of Mitchell discloses a cylindrical needle guard that surrounds and reciprocates along the barrel of a syringe. Locking of the needle guard is accomplished by interlocking between the guard and a collar mounted on the syringe barrel.

U.S. Pat. No. 4,655,751 of Harbaugh discloses another cylindrical extensible needle guard that surrounds the barrel of a syringe. Spaced ears on the inner surface of the guard engage similar spaced ears on the outer surface of the syringe barrel to temporarily lock the guard in selected longitudinal positions.

U.S. Pat. No. 4,664,654 of Strauss discloses a needle guard having a fixed cylindrical base member mounted over the forward end of the syringe barrel and a movable cylindrical guard member which telescopes from the base member about the needle. A manually moved knob extends from the guard member through a longitudinally extending slot in the base member. A coil spring inside the base member urges the guard member to its fully extended position in which the tip of the needle is enclosed and shielded.

U.S. Pat. No. 4,681,567 of Masters et al. discloses an open-ended cylindrical safety sheath that surrounds the barrel of a syringe and is longitudinally extensible with respect to the barrel. The sheath has an elongated slot formed therein.

U S. Pat. No. 4,702,738 of Spencer discloses yet another longitudinally reciprocating cylindrical sheath that surrounds the barrel of a syringe. Substantially axial guide channels are provided in the exterior of the barrel of the syringe and accept an inwardly projecting boss of the sheath to guide the same.

U.S. Pat. No. 4,7002,739 of Milorad discloses a combination holder and extensible sleeve for surrounding and enclosing a syringe and needle. The device is primarily intended as a guide facilitating insertion of the needle into the body part.

The aforementioned devices have not been successful in the medical field because they are unduly complex, require modifications to the basic syringe, are too expensive, or do not reliably prevent emergence of tip of the needle.

SUMMARY OF THE INVENTION

It is therefore the primary object of the present invention to provide an improved guard for a syringe that will protect the health care professional from inadvertently sticking himself or herself with the needle after administering medication or drawing blood with the syringe.

It is another object of the present invention to provide an improved disposable needle guard for a syringe.

It is another object of the present invention to provide an improved needle guard for a syringe that can be made of a unitary piece of injection molded plastic.

It is another object of the present invention to provide an improved guard which surrounds the barrel of a syringe and which may be retracted to expose the needle, extended to conceal the tip of the needle, and reliably locked in its extended position.

It is another object of the present invention to provide an improved sterilizable needle guard for a syringe.

It is another object of the present invention to provide an improved needle guard for a syringe which will give an audible signal to the user that it has been positioned to conceal the needle tip.

The present invention provides a guard for a syringe having an elongate cylindrical barrel and a needle extending from a forward end of the barrel. The guard includes an elongate generally cylindrical body portion dimensioned for surrounding and gripping the barrel of the syringe and adapted to slide longitudinally with respect to the barrel. A shield is connected to a forward end of the body portion for manual movement in a generally transverse direction with respect to a longitudinal axis of the needle. The shield can be moved to a use configuration to permit the needle to extend therebeyond when the body portion is slid to a retracted position. The shield can return to a non-use configuration in which a tip of the needle is concealed when the body portion is slid to an extended position.

The illustrated embodiments are injection molded as a single unitary piece of transparent polypropylene. The cylindrical body portion has a longitudinally extending slot so that it can be readily snapped around the barrel of the syringe. The shield is a spoon shaped member that can deflect transversely from an un-deflected non-use configuration to a slightly deflected in-use configuration to permit the needle to extend therebeyond when the guard is installed with the body portion in a retracted position relative to the barrel of the syringe. When the body portion of the guard is manually slid to an extended position relative to the syringe barrel, the spoon-shaped member returns to its un-deflected configuration and the tip of the needle is engaged by a plurality of ribs formed on an inner wall of the spoon-shaped member. The tip of the needle is thus concealed and accidental puncture is thereby is avoided.

BRIEF DESCRIPTION OF THE DRAWINGS

FIG. 1 is a plan view of a first embodiment of our syringe guard.

FIG. 2 is a side elevation view of the first embodiment of our syringe guard showing internal surfaces thereof in phantom lines.

FIG. 3 is an end elevation view of the first embodiment of our syringe guard taken from the bottom of FIG. 1.

FIG. 4 is a quarter sectional view of the first embodiment of our syringe guard taken along line 4—4 of FIG. 3.

FIG. 5 is a slightly reduced longitudinal sectional view of the first embodiment of our syringe guard illustrating the guard in its retracted position around syringe barrel and the forward shield member of the guard deflected to allow the needle to extend therebeyond for use.

FIG. 6 is a view similar to FIG. 5 with the guard extended on the syringe barrel and the tip of the needle of the syringe concealed inside the un-deflected shield member.

DESCRIPTION OF THE PREFERRED EMBODIMENTS

Figure 12:
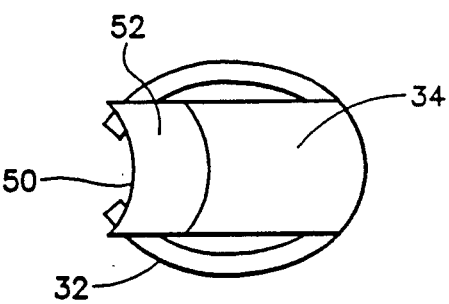
FIG. 12 is a top end elevation view of the second embodiment of our syringe guard.
Figure 7:
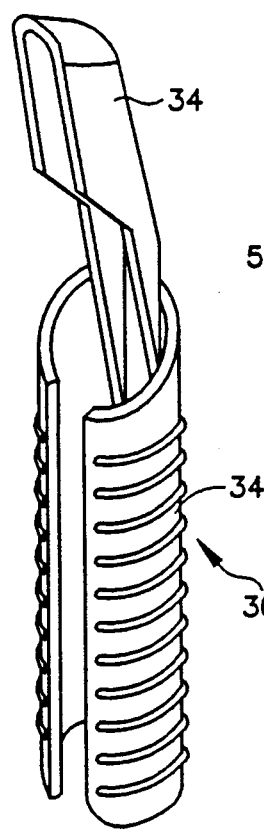
FIG. 7 is a perspective view of a second embodiment of our syringe guard.
Figure 8:
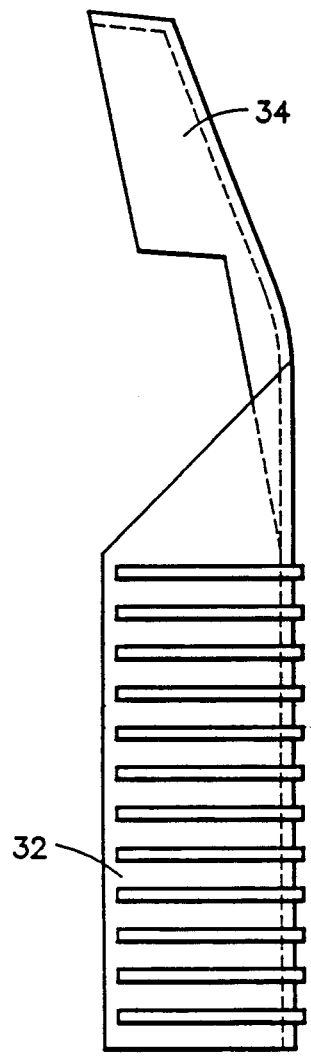
FIG. 8 is a side elevation view of the second embodiment of our syringe guard.

Referring to FIGS. 1 and 2, a first embodiment 10 of our syringe guard includes elongate cylindrical body portion 12 and a spoon-shaped shield member 14. The guard is injection molded as a single unitary piece of transparent polypropylene. Thus the guard is inexpensive and may be discarded with a syringe after use. Alternatively, the guard may be sterilized and re-used.

The cylindrical body portion has a longitudinally extending slot 16 (FIGS. 1 and 3) which extends the full length thereof. The slot allows the body portion 12 to expand slightly so that it can be readily snapped around the barrel 18 (FIG. 5) of a syringe. As best seen in FIG. 3, the cross-sectional shape of the body portion 12 may be slightly oval before it is installed around the barrel of the syringe. This increases the gripping force once installed.

The spoon-shaped member 14 normally extends from the forward end of the body portion 12 with the un-deflected configuration illustrated in FIG. 2. This shield member 14 can deflect transversely from a non-use un-deflected configuration illustrated in FIGS. 2 and 6 to a slightly bent or deflected in-use configuration illustrated in FIG. 5 to permit a needle 20 of the syringe to extend therebeyond. This occurs when the guard 10 is first installed with the body portion 12 in a retracted position (FIG. 5) relative to the barrel 18 of the syringe. The intermediate segment of the needle 20 then rests in a recess 22a (FIGS. 1 and 3) in a forward wall 22 of the shield member 14. The edge of this recess presses tightly against the intermediate segment of the needle 20.

When the body portion 12 of the guard is manually slid to an extended position (FIG. 6) relative to the syringe barrel, the sharp tip or distal end 20a (FIG. 5) of the needle 20 then snaps past the inner edge of the wall 22 of the spoon-shaped member 14. The member immediately returns to its un-deflected configuration (FIG. 6) as a result of the elastic memory in the plastic. The tip 22a simultaneously engages and moves past, in ratchet-like fashion, one or more of a plurality of transversely extending ribs 24 (FIG. 2) formed on an inner surface of the wall 22 of the spoon-shaped member 14. The ribs serve to lock the shield member 14 in place over the sharp tip 22a of the needle. The tip of the needle is thus reliably concealed and accidental puncture thereby is avoided when the syringe is further handled and transported.

An exterior surface of the body portion 12 opposite the slot 16 is formed with a plurality of serrations 26 (FIGS. 2 and 5) to facilitate non-slip engagement by the fingers or thumb of a health care profession. This facilitates manually moving the body portion 12 between its extended and retracted positions with respect to the barrel 18 of the syringe. These serrations are illustrated in phantom lines in FIG. 4.

Referring to FIGS. 7 through 10, a second embodiment 30 of our syringe guard also includes elongate cylindrical body portion 32 and a spoon-shaped shield member 34. Again this guard is preferably injection molded as a single unitary piece of transparent polypropylene.

Figure 9:
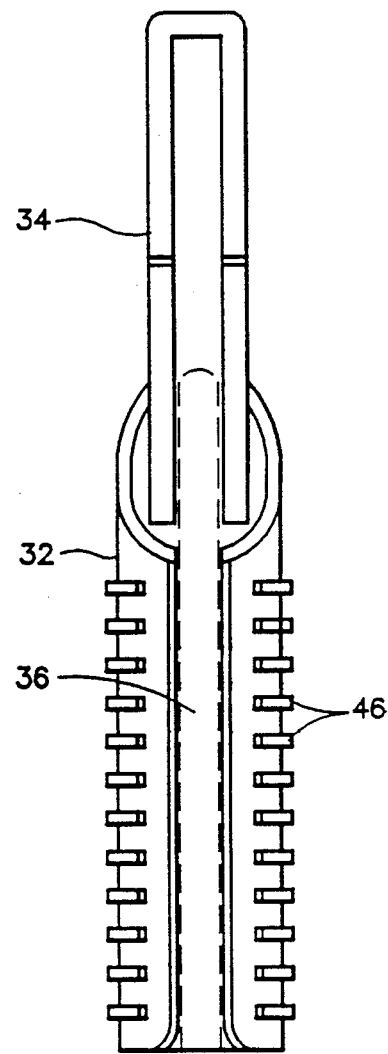
FIG. 9 is a top plan view of the second embodiment of our syringe guard.
Figure 13:
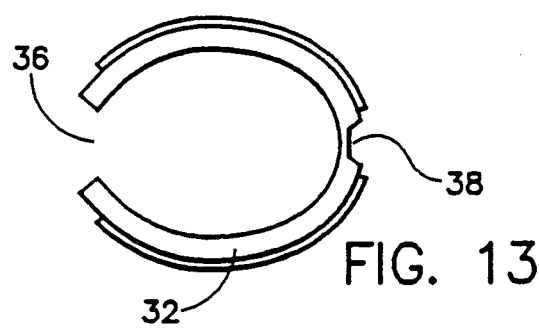
FIG. 13 is a cross-section view of the second embodiment of our syringe guard taken along line A—A of FIG. 11.
Figure 10:
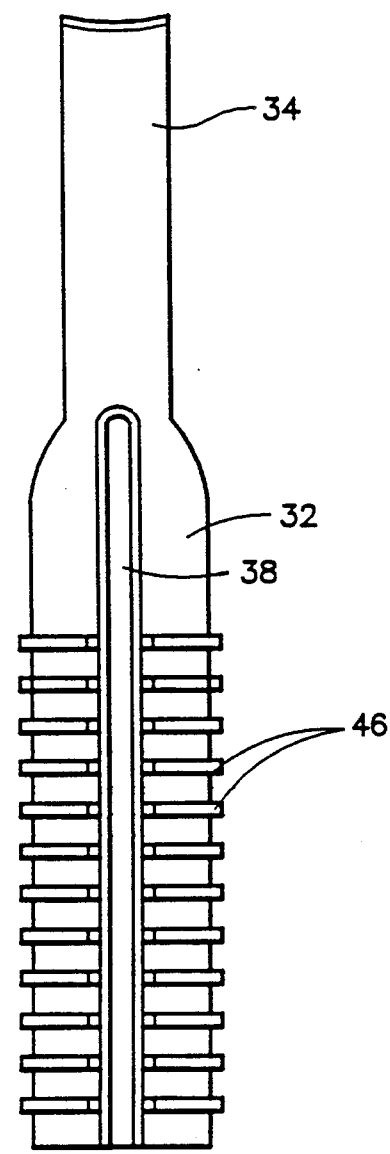
FIG. 10 is a bottom plan view of the second embodiment of our syringe guard.

The cylindrical body portion 32 has a longitudinally extending slot 36 (FIG. 9) which extends the full length thereof. The slot allows the body portion 32 to expand slightly so that it can be snapped around the barrel of a syringe in a similar manner as the first embodiment. As best seen in FIG. 10, a longitudinally extending recess 38 is formed in the cylindrical body portion 32, opposite the slot 36, for facilitating the expansion of the circumferential half sections of the cylindrical body portion around the syringe barrel. Referring to FIG. 13, the cross-sectional shape of the body portion 32 is slightly oval before it is installed around the barrel of the syringe. This increases the gripping force once installed.

Figure 14:
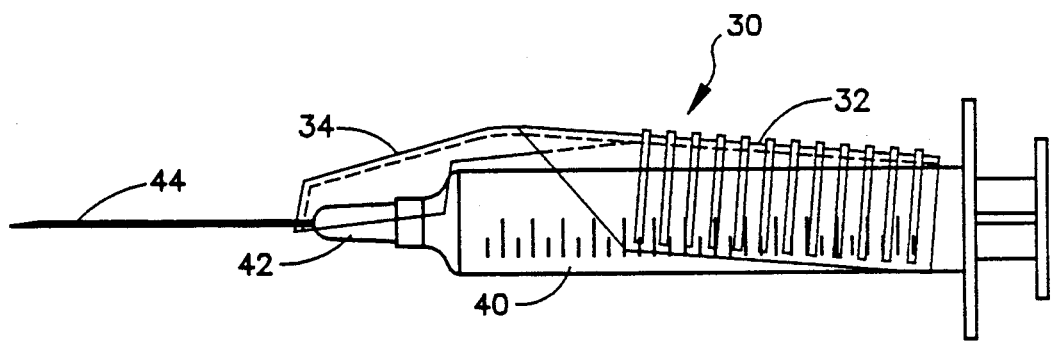
FIG. 14 is a diagrammatic view of the second embodiment with the guard retracted on the syringe barrel and the shield member engaged with the hub attachment section of the syringe.
Figure 15:
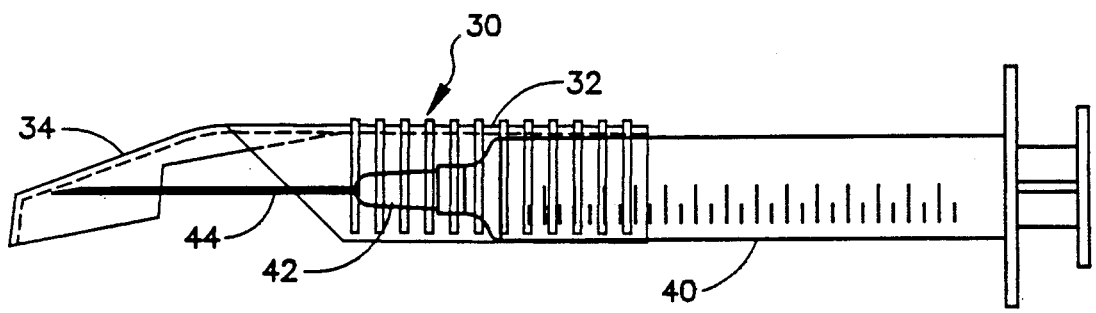
FIG. 15 is a diagrammatic view similar to FIG. 14 with the guard extended on the syringe barrel and the tip of the needle of the syringe concealed inside the un-deflected shield member.

FIG. 14 is a diagrammatic view of the second embodiment of the guard 30 retracted on a syringe barrel 40. The shield member 34 is engaged with and abuts the hub attachment section 42 of the syringe at the rear or base end of the needle 44. FIG. 15 is a diagrammatic view similar to FIG. 14 with the guard extended on the syringe barrel and the forward tip of the needle 44 concealed inside the un-deflected shield member 34. The shield member 34 can move transversely from a deflected in-use configuration illustrated in FIG. 14 to a non-use un-deflected configuration illustrated in FIG. 15. In the deflected configuration the tip of the needle 44 extends beyond the end of the shield member 34. In our second embodiment, the shield member 34 need not bend as in the first embodiment, instead the transverse or lateral deflection relative to the syringe is accomplished by varying the angular position of the cylindrical body portion 32 on the syringe barrel. Sidewalls 45 (FIG. 11) of the shield member rigidly connect to the forward end of the body portion 32 in cantilevered fashion.

Figure 11:
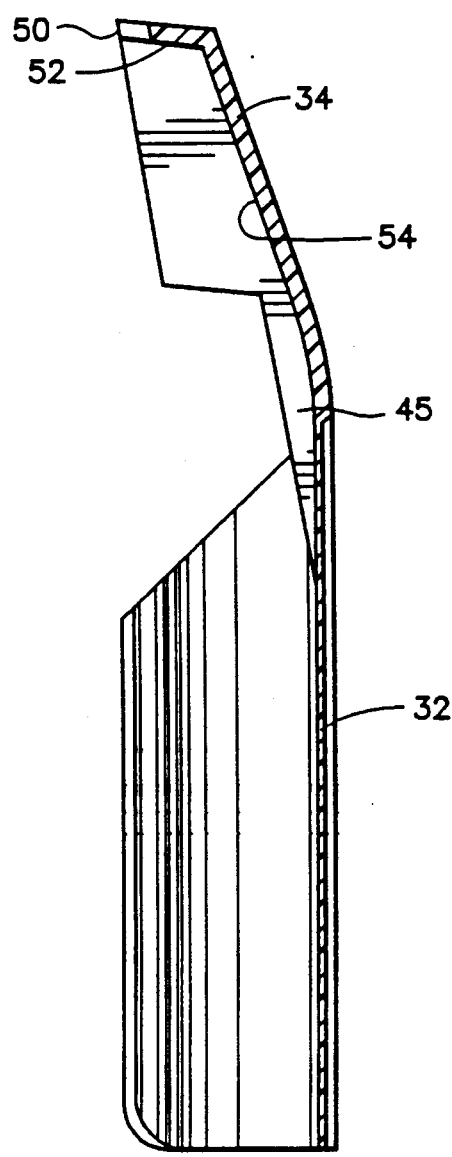
FIG. 11 is a longitudinal sectional view of the second embodiment of our syringe guard.

The guard 30 may be installed with the body portion 32 in a retracted position (FIG. 14) relative to the barrel 40 of the syringe. The needle cap (not illustrated) may then be removed from the tip of the needle 44 and the syringe filled with vaccine from a vial. Once the injection into the patient has been completed, the health care professional slides the guard forwardly on the barrel with the aid of circumferential serrations or ribs 46 (FIGS. 9 and 11). These ribs extend radially outwardly from the cylindrical body portion 32 and facilitate non-slip gripping of the guard. The cylindrical body portion 32 extends more than half the length of the barrel 40 of the syringe. As best seen in FIGS. 9 and 12, the shield member 34 has a relatively narrow box-like shape. The shield member is sufficiently narrow so that it will ride on the hub attachment section 42 (FIG. 14) of the syringe and will not move transversely so as to enclose the same.

When the guard 30 is slid forwardly on the syringe barrel enough to push the sidewalls 45 (FIG. 11) of the shield member 34 past the hub attachment section, the spring force of the cylindrical body portion will cause the shield member to move toward the axis of the needle 44. This spring force is the result of the fact that when the body portion 32 extends tangentially to the syringe barrel as in FIG. 14, the same is over-spread against its plastic memory. When the shield member 34 moves against the needle 44, an intermediate segment of the needle rests against an arcuate upper edge 50 (FIG. 12) of the forward wall 52 of the shield member. Continued forward pushing of the guard 30 results in further transverse movement of the shield member under the residual stored spring force of the cylindrical body portion 32. The tip of the needle 44 ends up being concealed behind the forward wall 52. The spring action is sufficient so that the needle strikes the bottom wall 54 (FIG. 11) of the shield member 34 with enough force to make a snap sound. This provides an audible signal to the health care professional that the tip of the needle is now safely concealed.

While we have illustrated and described two embodiments of our needle guard for a syringe, it should be understood that it can be modified in arrangement and detail. For example, the tip engaging ribs could be replaced with a sponge material or some other needle tip retaining means. The guard could be molded in a variety of color coded sizes. Therefore, the protection afforded our invention should only be limited in accordance with the scope of the following claims.

We claim:

1. A guard for a syringe having an elongate cylindrical barrel, a needle, and a hub attachment section connecting a reward end of the needle to a forward end of the barrel, comprising:
   elongated substantially rigid shield means for enclosing a forward tip of the needle; and
   elongated body means connected directly to the shield means for surrounding the barrel and sliding longitudinally therealong from a retracted position angularly disposed relative to the barrel to an extended position substantially parallel to the barrel in which the shield means encloses the tip of the needle, the body means providing a spring force when in its retracted position that urges the shield means against the needle, said spring force being provided by over-spread of a pair of circumferential half-sections of a generally cylindrical body portion having a longitudinally extending slot, the body portion further having a longitudinally extending recess opposite the slot to facilitate spreading of the circumferential half-sections.

2. A guard for a syringe according to claim 1 wherein an exterior surface of the body portion is formed with a plurality of serrations to facilitate non-slip engagement by the fingers or thumb of a health care professional who is manually moving the body means between its extended and retracted positions with respect to the barrel of the syringe.

3. A guard for a syringe according to claim 1 wherein the shield means comprises a generally spoon-shaped member extending from a forward end of the body portion.

4. A guard for a syringe according to claim 1 wherein the shield means includes retaining means for engaging the tip of the needle when the body means is in its extended position to thereby conceal the tip and prevent accidental puncture thereby.

5. A guard for a syringe according to claim 1 the shield means can move transversely from a deflected in-use configuration to an undeflected non-use configuration.

6. A guard for a syringe according to claim 1 wherein the shield means and the body means are formed of a single unitary piece of plastic.

7. A guard for a syringe according to claim 6 wherein the plastic is clear polypropylene.

8. A guard for a syringe according to claim 1 wherein the shield means is a member connected to the forward end of the body portion and bendable into and out of obstructing relationship with the tip of the needle.

9. A guard for a syringe according to claim 1 wherein the shield means is a member connected to the forward end of the body portion and is deflectable into and out of obstructing relationship with the tip of the needle under the spring force provided by the over-spread of the circumferential half-sections.

10. A guard for a syringe according to claim 1 wherein the spring force is sufficient to cause the shield means to strike the needle with sufficient force when the body means is slid to its extended position to create an audible snap noise.

* * * * *